United States Patent [19]

Lamont

[11] Patent Number: Plant 7,546

[45] Date of Patent: Jun. 4, 1991

[54] *LESCHENAULTIA FORMOSA* VARIETY 'STARBURST'

[75] Inventor: Gregory P. Lamont, Wyoming, Australia

[73] Assignee: Ornamental Native Australian Plants Pty Ltd, Armidale, Australia

[21] Appl. No.: 427,594

[22] Filed: Oct. 26, 1989

[30] Foreign Application Priority Data

Oct. 31, 1988 [AU] Australia ..... 88/032

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Ernest M. Anderson

[57] ABSTRACT

A new and distinct variety of *Leschenaultia formosa* characterized by the combination of a large flower with predominantly red petals, and a yellow center and a corolla tube which is predominantly maroon externally.

1 Drawing Sheet

ORIGIN OF THE VARIETY

This variety arises from the controlled pollination in November 1986 at the Horticultural Research Station, Gosford New South Wales Australia, of a commercial variety of *L. formosa* "Sunrise" by a collected *L. formosa* plant with orange/red flowers and a prostrate growth form Breeders Accession No. 4. Seeds were germinated and a seedling was selected for flowering duration and the size and color of its flowers. Subsequent plants have been propagated asexually from that seedling by tissue culture and stem cuttings. The subsequent plants produced possess all the characteristics or come true to form with the original plant and the characteristic features are firmly fixed and maintained in the succeeding generations of plants.

SUMMARY OF THE VARIETY

"Starburst" is a small bushy prostrate herbaceous perennial plant to 10.0 cm tall. The foliage is dense with small green fleshy leaves crowding the stems. The flowering season of "Starburst" is from April to October in the southern hemisphere. Flowering occurs in a cyclical and frequent pattern throughout the year in protected cultivation. The fanshaped flowers are large, mean 30.6 mm wide×mean 22.1 mm high, with the petals being predominantly red with a yellow center. The corolla tube is predominantly maroon externally. "Starburst" is fertile and is suitable as a potted flowering ornamental.

DESCRIPTION OF THE PHOTOGRAPHS

The accompanying photographs show typically:

(i) the plant form and size and the display of flowers;
(ii) the size and color of the perianth of "Starburst" (left) relative to "Sunrise".

The colors are as nearly true as reasonably possible in color representations of this type.

DESCRIPTION OF THE VARIETY

In the following botanical description colour references are made to The Royal Horticultural Society Colour Chart. Descriptions are based on observations made during August 1988 of 20 randomly selected, 12 month old well-fertilized potted plants growing in an open sided unheated polyethylene greenhouse at the Horticultural Research Station, Gosford New South Wales Australia.

Name: "Starburst".
Botanical name: *Leschenaultia formosa* Goodeniaceae.
Commercial use: Potted flowering ornamental plant.
Form: Small and prostrate.
Plant characteristics:

- *Height at 4–12 months.*—To 10 cm.
- *Growth habit.*—Prostrate.
- *Life cycle.*—Herbaceous perennial.
- *Foliage.*—Very dense.
- *Stem color.*—144B yellow green.
- *Leaf.*—Length: Mean 8.2 mm; Range 6.8–9.2 mm. Width: Mean 0.75 mm; Range 0.5–1.1 mm. Color: 137A green.
- *Flowering season.*—Cyclical and frequent through the year.
- *Flower.*—Width: Mean 30.6 mm; Range 28.0–34.2 mm. Height: Mean 22.1 mm; Range 21.0–24.4 mm.
- *Corolla length from base to petal split.*—Mean 15.03 mm; Range 13.8–16.0 mm.
- *Ovary length.*—Mean 14.31 mm; Range 12.5–15.9 mm.
- *Corolla tube.*—Main color (external): 59A maroon.
- *Petal color.*—Red and Yellow. Just open: 45A margin, 32A body; 17A center. fully open: 46A margin, 33A body; 15A center. aged: 46A outer; 15B center.

COMPARISONS WITH OTHER KNOWN SIMILAR VARIETIES OF LESCHENAULTIA

The seed parent *L. formosa* "Sunrise" is an acknowledged variety of the New South Wales nursery trade and is the nearest commercially known available variety.

The observations for the comparison were made under the same circumstances as those for the Description of the Variety.

"Starburst" has petal colors when fully open of 46A red margin, 33A orange/red body and 15A yellow center and "Sunrise" has petal colors when fully open of 45B red margin and 17A yellow/orange center.

"Starburst" has a flower width of mean 30.6 mm while the flower width of "Sunrise" is mean 20.3 mm.

"Starburst" has a flower height of mean 22.1 mm while the flower height of "Sunrise" is mean 15.4 mm.

I claim the following:

1. A new and distinct variety of *Leschenaultia formosa* plant characterized by the combination of a large flower with predominantly red petals and a yellow center, and a corolla tube which is predominantly maroon externally.

* * * * *

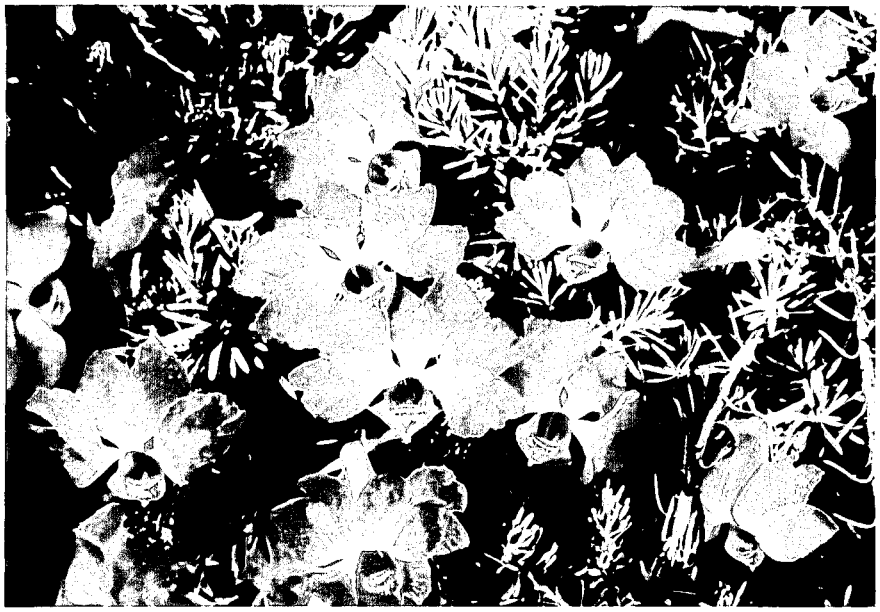
i)
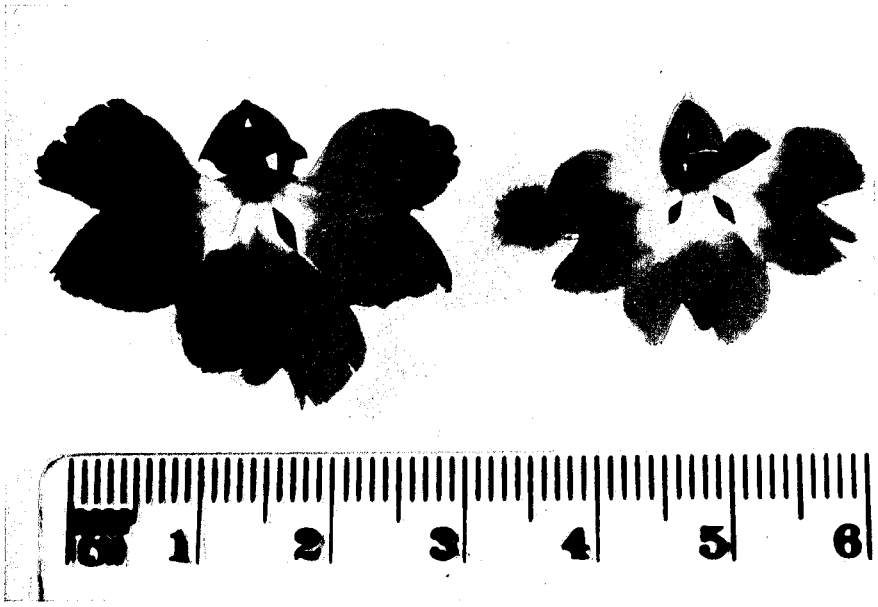
ii)